US012205582B2

(12) United States Patent
Scholl et al.

(10) Patent No.: US 12,205,582 B2
(45) Date of Patent: Jan. 21, 2025

(54) SYSTEM AND METHOD FOR IMPLEMENTING A VIRTUAL CAREGIVER

(71) Applicant: MASTERCARD INTERNATIONAL INCORPORATED, Purchase, NY (US)

(72) Inventors: Christopher T. Scholl, Saint Peters, MO (US); Shawn Mehrhoff, Saint Ann, MO (US); James W. Barkhurst, Fenton, MO (US)

(73) Assignee: MASTERCARD INTERNATIONAL INCORPORATED, Purchase, NY (US)

(*) Notice: Subject to any disclaimer, the term of this patent is extended or adjusted under 35 U.S.C. 154(b) by 647 days.

(21) Appl. No.: 17/496,706

(22) Filed: Oct. 7, 2021

(65) Prior Publication Data

US 2022/0115126 A1 Apr. 14, 2022

Related U.S. Application Data

(60) Provisional application No. 63/089,319, filed on Oct. 8, 2020.

(51) Int. Cl.
*G10L 15/22* (2006.01)
(52) U.S. Cl.
CPC .................................... *G10L 15/22* (2013.01)
(58) Field of Classification Search
CPC ......... G10L 15/22; G10L 25/78; G16H 20/10; G16H 20/70; G16H 40/67; G08B 21/24
See application file for complete search history.

(56) References Cited

U.S. PATENT DOCUMENTS 5,612,869 A 3/1997 Letzt et al.
5,625,864 A 4/1997 Budow et al.
(Continued)

FOREIGN PATENT DOCUMENTS

EP 1304671 B1 3/2006
WO 2001086609 A1 11/2001
(Continued)

OTHER PUBLICATIONS

"LifePod Giving Voice to Caregivers", Webpage, LifePod Solutions, 2019, 4 pages, archived online on Jan. 18, 2019 at URL: https://web.archive.org/web/20190118210401/https://lifepod.com/.
(Continued)

*Primary Examiner* — Fariba Sirjani
(74) *Attorney, Agent, or Firm* — Armstrong Teasdale LLP

(57) ABSTRACT

A virtual caregiver (VC) computing device may be provided. The VC computing device may include at least one processor in communication with at least one memory device, at least one sensor, and a payment processing network. The at least one processor may be configured to receive task data, generate, based on the task data, a task including a task identifier, a fulfillment condition, and a time deadline, store the generated task in a task database, receive, from the at least one sensor, sensor data, retrieve, from the payment processing network, transaction data, compare at least one of the received sensor data and the retrieved transaction data to the fulfillment condition to determine that the fulfillment condition has occurred, and record, in the task database, the task as fulfilled based on the determination that the fulfillment condition has occurred.

20 Claims, 9 Drawing Sheets

(56) References Cited

U.S. PATENT DOCUMENTS

| | | | |
|---|---|---|---|
| 5,792,204 A | 8/1998 | Snell | |
| 6,721,704 B1 | 4/2004 | Strubbe et al. | |
| 7,573,371 B1 | 8/2009 | Miller | |
| 7,825,794 B2 | 11/2010 | Janetis et al. | |
| 7,978,085 B1 | 7/2011 | Kearns et al. | |
| 8,234,289 B2 | 7/2012 | Abernethy, Jr. et al. | |
| 8,408,208 B2* | 4/2013 | Bacon | A61M 15/008 128/200.14 |
| 8,447,654 B1 | 5/2013 | Argue et al. | |
| 8,712,760 B2 | 4/2014 | Hsia et al. | |
| 8,817,951 B2 | 8/2014 | Goffin et al. | |
| 8,977,390 B2* | 3/2015 | Jefferies | G06Q 20/10 700/237 |
| 9,208,661 B2 | 12/2015 | Junqua et al. | |
| 9,378,734 B2 | 6/2016 | Ganong, III et al. | |
| 9,396,632 B2 | 7/2016 | Brav et al. | |
| 9,408,996 B2 | 8/2016 | Pompilio, III et al. | |
| 9,514,281 B2 | 12/2016 | Hirst et al. | |
| 9,536,049 B2 | 1/2017 | Brown et al. | |
| 9,589,107 B2 | 3/2017 | Bowers et al. | |
| 9,786,145 B2 | 10/2017 | Oppenheimer | |
| 9,786,148 B2 | 10/2017 | Sundaram et al. | |
| 9,837,067 B2 | 12/2017 | Kleiss et al. | |
| 9,954,156 B2 | 4/2018 | Jogia | |
| 9,959,775 B2 | 5/2018 | Pracar et al. | |
| 10,019,987 B2 | 7/2018 | Dides et al. | |
| 10,121,070 B2 | 11/2018 | Derenne et al. | |
| 10,134,395 B2 | 11/2018 | Typrin | |
| 10,135,965 B2 | 11/2018 | Woolsey et al. | |
| 10,152,988 B2 | 12/2018 | Kim et al. | |
| 10,158,728 B1 | 12/2018 | VanBlon et al. | |
| 10,834,562 B1* | 11/2020 | Zalewski | H04W 4/80 |
| 10,841,724 B1* | 11/2020 | Tran | G06F 3/013 |
| 2001/0032085 A1 | 10/2001 | Goedeke et al. | |
| 2002/0103647 A1 | 8/2002 | Houplain | |
| 2002/0150869 A1* | 10/2002 | Shpiro | G09B 7/02 434/156 |
| 2003/0039345 A1 | 2/2003 | Yang et al. | |
| 2003/0050731 A1* | 3/2003 | Rosenblum | G07F 17/0092 700/232 |
| 2003/0052787 A1 | 3/2003 | Zerhusen et al. | |
| 2003/0125945 A1 | 7/2003 | Doyle | |
| 2005/0057361 A1 | 3/2005 | Giraldo et al. | |
| 2005/0075542 A1 | 4/2005 | Goldreich | |
| 2005/0086082 A1 | 4/2005 | Braunstein et al. | |
| 2005/0288721 A1 | 12/2005 | Girouard et al. | |
| 2006/0288225 A1 | 12/2006 | Jung et al. | |
| 2007/0057798 A1 | 3/2007 | Li et al. | |
| 2007/0127640 A1* | 6/2007 | Brunel | H04L 51/08 704/E15.045 |
| 2007/0253021 A1 | 11/2007 | Mehta et al. | |
| 2008/0059228 A1* | 3/2008 | Bossi | G16H 30/20 705/2 |
| 2008/0082338 A1 | 4/2008 | ONeil et al. | |
| 2008/0154099 A1 | 6/2008 | Aspel et al. | |
| 2008/0165286 A1 | 7/2008 | Oh et al. | |
| 2008/0294462 A1 | 11/2008 | Nuhaan et al. | |
| 2009/0099848 A1 | 4/2009 | Emner et al. | |
| 2009/0259728 A1 | 10/2009 | Berisford et al. | |
| 2009/0294339 A1 | 12/2009 | Biewer et al. | |
| 2010/0131280 A1 | 5/2010 | Bogineni | |
| 2010/0269049 A1 | 10/2010 | Fearon | |
| 2010/0286490 A1* | 11/2010 | Koverzin | G08B 21/0492 704/231 |
| 2011/0282671 A1 | 11/2011 | Dicks et al. | |
| 2012/0166322 A1 | 6/2012 | Simon | |
| 2012/0198259 A1 | 8/2012 | Williams et al. | |
| 2013/0147899 A1 | 6/2013 | Labhard | |
| 2013/0150686 A1 | 6/2013 | Fronterhouse et al. | |
| 2013/0179173 A1 | 7/2013 | Lee et al. | |
| 2013/0185068 A1* | 7/2013 | Tanaka | G10L 15/08 704/233 |
| 2013/0211291 A1* | 8/2013 | Tran | A61B 5/1116 600/595 |
| 2013/0267795 A1 | 10/2013 | Cosentino et al. | |
| 2014/0062697 A1* | 3/2014 | Ramaswamy | H04L 51/224 340/540 |
| 2014/0074464 A1 | 3/2014 | Berens | |
| 2014/0168453 A1 | 6/2014 | Shoemake et al. | |
| 2014/0214426 A1 | 7/2014 | Kanevsky et al. | |
| 2014/0257852 A1 | 9/2014 | Walker et al. | |
| 2015/0035675 A1 | 2/2015 | Gunaratnam et al. | |
| 2015/0056588 A1 | 2/2015 | Bayer | |
| 2015/0094830 A1 | 4/2015 | Lipoma et al. | |
| 2015/0149171 A1 | 5/2015 | Goldman et al. | |
| 2015/0185752 A1 | 7/2015 | Bard et al. | |
| 2015/0269827 A1 | 9/2015 | Hopkins et al. | |
| 2015/0295784 A1 | 10/2015 | Kim et al. | |
| 2015/0327691 A1* | 11/2015 | Alshammari | A47F 1/04 312/7.2 |
| 2015/0331666 A1 | 11/2015 | Bucsa et al. | |
| 2015/0356836 A1 | 12/2015 | Schlesinger et al. | |
| 2016/0039424 A1 | 2/2016 | Hong et al. | |
| 2016/0041811 A1 | 2/2016 | Parundekar et al. | |
| 2016/0052391 A1 | 2/2016 | Walsh et al. | |
| 2016/0094812 A1 | 3/2016 | Chen | |
| 2016/0100092 A1 | 4/2016 | Bohac | |
| 2016/0164813 A1 | 6/2016 | Anderson et al. | |
| 2016/0307258 A1* | 10/2016 | May | G06Q 30/0635 |
| 2016/0334866 A9 | 11/2016 | Mazed et al. | |
| 2016/0345914 A1 | 12/2016 | Jain | |
| 2016/0371620 A1 | 12/2016 | Nascenzi et al. | |
| 2017/0053088 A1 | 2/2017 | Walker et al. | |
| 2017/0074717 A1* | 3/2017 | Pilkington | G01G 21/22 |
| 2017/0160813 A1 | 6/2017 | Divakaran et al. | |
| 2017/0213191 A1 | 7/2017 | Pitcher | |
| 2017/0372592 A1 | 12/2017 | Neravati et al. | |
| 2018/0004909 A1 | 1/2018 | Cronin et al. | |
| 2018/0018373 A1 | 1/2018 | Yazdian et al. | |
| 2018/0211656 A1 | 7/2018 | Chong et al. | |
| 2018/0218636 A1 | 8/2018 | Alaouf et al. | |
| 2018/0260680 A1 | 9/2018 | Finkelstein et al. | |
| 2018/0296092 A1 | 10/2018 | Hassan et al. | |
| 2018/0325469 A1 | 11/2018 | Fountaine | |
| 2018/0325470 A1* | 11/2018 | Fountaine | G08B 21/0446 |
| 2018/0342329 A1* | 11/2018 | Rufo | G16H 40/67 |
| 2018/0366143 A1 | 12/2018 | Ashoori et al. | |
| 2019/0009049 A1 | 1/2019 | Candy | |
| 2019/0019077 A1 | 1/2019 | Griffin et al. | |
| 2019/0043622 A1 | 2/2019 | Ramaci | |
| 2019/0096534 A1 | 3/2019 | Joao | |
| 2019/0252079 A1* | 8/2019 | Constantin | A61B 5/14532 |
| 2019/0266874 A1 | 8/2019 | Baker et al. | |
| 2019/0362740 A1* | 11/2019 | Hauptman | G10L 17/26 |
| 2020/0382451 A1* | 12/2020 | Ogawa | G06F 3/015 |

FOREIGN PATENT DOCUMENTS

| | | |
|---|---|---|
| WO | 2005065216 A2 | 7/2005 |
| WO | 2016097368 A1 | 6/2016 |
| WO | 2016127185 A1 | 8/2016 |
| WO | 2017036516 A1 | 3/2017 |
| WO | 2018023990 A1 | 2/2018 |
| WO | 2018094226 A1 | 5/2018 |
| WO | 2018229592 A1 | 12/2018 |

OTHER PUBLICATIONS

Clark, Jay, "Using the Amazon Echo to improve the lives of Alzheimer's patients", Medium, May 16, 2017, 10 pages, accessed online at URL: https://medium.com/@JaysThoughts/using-the-amazon-echo-to-improve-the-lives-of-alzheimers-patients-f5727560a5eb.

Coombs, Bertha, "How Alexa's best skill could be as a home health-care assistant", CNBC LLC, May 16, 2017, 8 pages, accessed online at URL: https://www.cnbc.com/2017/08/09/how-alexas-best-skill-could-be-as-a-home-health-care-assistant.html.

Johnston, Lucy, "For people with dementia, virtual reality can be life-changing", WIRED, May 21, 2018, 4 pages, accessed online at URL: https://www.wired.co.uk/article/virtual-reality-dementia-technology.

(56) References Cited

OTHER PUBLICATIONS

Kegel, Magdalena, "Daily-living Virtual Assistant That Reads Emotions Being Developed for Alzheimer's Patients", Alzheimer's News Today, Sep. 6, 2017, 8 pages, accessed online at URL: https://alzheimersnewstoday.com/2017/09/06/canadians-developing-virtual-assistant-for-alzheimers-patients-that-can-read-emotions/.

Ledain, Timon, "Meet LifePod, Your Amazon Alexa Powered Virtual Caregiver", Macadamian, Nov. 9, 2016, 5 pages, accessed online at URL: https://www.macadamian.com/learn/amazon-alexa-powered-virtual-caregiver/.

Mohney, Gillian, "Researchers Create 'Alexa-Like' Assistant to Help Alzheimer's Patients", Healthline Media, Sep. 7, 2017, 6 pages, accessed online at URL: https://www.healthline.com/health-news/alexa-like-assistant-to-help-alzheimers-patients#1.

Orlov, Laurie, "'Alexa, tell my nurse I need help.' RCare Announces Integration", Aging and Health Technology Watch, Jul. 12, 2018, 2 pages, accessed online at URL: https://www.ageinplacetech.com/pressrelease/alexa-tell-my-nurse-i-need-help-rcare-announces-integration.

Regan, Tim, "Virtual Assistant in Development Could Help Alzheimer's Patients at Home", Home Health Care News, Aug. 31, 2017, 5 pages, accessed online at URL: https://homehealthcarenews.com/2017/08/new-virtual assistant-could-help-alzheimers-patients-at-home/.

Sarmah-Hightower, Satta, "Alexa, Will You Help My Mom's Caregiver?", Care.com, Feb. 14, 2018, 4 pages, accessed online at URL: https://www.care.com/c/stories/12827/amazon-alexa-will-you-be-my-moms-senior-caregiver/.

Stempak, Nicole, "A virtual assistant to help people with Alzheimer's disease", IASC, Plain-English Health Care, Aug. 31, 2017, 4 pages, accessed online at URL: https://www.iadvanceseniorcare.com/news-item/memory-care/virtual-assistant-help-people-alzheimers-disease.

Strohbusch, Beth, "Libertana Home Health Deploys Orbita Voice Experience Software to Provide Amazon Echo-based Digital Care Assistants in Community-Based Housing Environments", Cision, Aug. 10, 2017, 3 pages, accessed online at URL: https://www.prweb.com/releases/2017/08/prweb14593629.htm.

"OnGuardian", Webpage, Amazon.com, retrieved on Oct. 7, 2021 from URL: https://www.amazon.com/OnGuardian-Apps-LLC/dp/B06XGTJ549.

\* cited by examiner

SYSTEM AND METHOD FOR IMPLEMENTING A VIRTUAL CAREGIVER

CROSS-REFERENCE TO RELATED APPLICATIONS

This application claims the benefit of priority to U.S. Provisional Patent Application No. 63/089,319, filed Oct. 8, 2020, the entire contents and disclosure of which are hereby incorporated by reference in their entirety.

BACKGROUND

This disclosure relates generally to virtual assistance systems, and more specifically, to a system and method for implementing a virtual caregiver.

Some patients, such as dementia patients, may have difficulty remembering tasks they must perform. For example, patients are often responsible for taking prescribed medications, purchasing food, paying bills, maintaining personal hygiene, and/or other tasks that must be performed periodically but may be forgotten by some patients. Caregivers are often responsible for prompting or otherwise reminding such patients to perform these tasks. However, because caregivers often cannot be constantly present with the patient, caregivers may be unable to know which tasks the patient has or has not remembered to perform or to give timely reminders to the patient. Further, some patients may have difficulty in speaking or remembering ideas (e.g., past stories or observations), which may cause frustration on the part of the patient, caregivers, and other listeners.

A system that provides a virtual caregiver that enables remote tracking of tasks to be performed by patients is therefore desirable.

BRIEF DESCRIPTION

In one aspect, a virtual caregiver (VC) computing device is provided. The VC computing device may include at least one processor in communication with at least one memory device, at least one sensor, and a payment processing network. The at least one processor may be configured to receive task data. The at least one processor may further be configured to generate, based on the task data, a task including a task identifier, a fulfillment condition, and a time deadline. The at least one processor may further be configured to store the generated task in a task database. The at least one processor may further be configured to receive, from the at least one sensor, sensor data. The at least one processor may further be configured to retrieve, from the payment processing network, transaction data. The at least one processor may further be configured to compare at least one of the received sensor data and the retrieved transaction data to the fulfillment condition to determine that the fulfillment condition has occurred. The at least one processor may further be configured to record, in the task database, the task as fulfilled based on the determination that the fulfillment condition has occurred.

In another aspect, a computer-implemented method for implementing a virtual caregiver (VC) is provided. The computer-implemented method may be performed by a VC computing device including at least one processor in communication with at least one memory device, at least one sensor, and a payment processing network. The computer-implemented method may include receiving, by the VC computing device, task data. The computer-implemented method may further include generating, by the VC computing device, based on the task data, a task including a task identifier, a fulfillment condition, and a time deadline. The computer-implemented method may further include storing, by the VC computing device, the generated task in a task database. The computer-implemented method may further include receiving, by the VC computing device, from the at least one sensor, sensor data. The computer-implemented method may further include retrieving, by the VC computing device, from the payment processing network, transaction data. The computer-implemented method may further include comparing, by the VC computing device, at least one of the received sensor data and the retrieved transaction data to the fulfillment condition to determine that the fulfillment condition has occurred. The computer-implemented method may further include recording, by the VC computing device, in the task database, the task as fulfilled based on the determination that the fulfillment condition has occurred.

In another aspect, at least one non-transitory computer-readable media having computer-executable instructions embodied thereon may be provided. When executed by a virtual caregiver (VC) computing device including at least one processor in communication with at least one memory device, at least one sensor and a payment processing network, the computer-executable instructions may cause the at least one processor to receive task data. The computer-executable instructions may further cause the at least one processor to generate, based on the task data, a task including a task identifier, a fulfillment condition, and a time deadline. The computer-executable instructions may further cause the at least one processor to store the generated task in a task database. The computer-executable instructions may further cause the at least one processor to receive, from the at least one sensor, sensor data. The computer-executable instructions may further cause the at least one processor to retrieve, from the payment processing network, transaction data. The computer-executable instructions may further cause the at least one processor to compare at least one of the received sensor data and the retrieved transaction data to the fulfillment condition to determine that the fulfillment condition has occurred. The computer-executable instructions may further cause the at least one processor to record, in the task database, the task as fulfilled based on the determination that the fulfillment condition has occurred.

BRIEF DESCRIPTION OF THE DRAWINGS

FIG. 1 is a schematic diagram illustrating an exemplary virtual caregiver (VC) system according to one example embodiment of the present disclosure.

FIG. 2 is a data flow diagram illustrating an exemplary data flow within the VC system illustrated in FIG. 1 according to one example embodiment of the present disclosure.

FIG. 3 is an example configuration of a client system, in accordance with one embodiment of the present disclosure.

FIG. 4 illustrates an example configuration of a server system, in accordance with one embodiment of the present disclosure.

FIG. 5 illustrates an example configuration of a VC computing device shown in FIG. 1, in accordance with one embodiment of the present disclosure.

FIG. 6 is a flowchart of a computer-implemented method for implementing a VC, which may be implemented using the system shown in FIG. 1.

FIG. 7 is a continuation of the flowchart shown in FIG. 6.

FIG. 8 is a continuation of the flowchart shown in FIG. 7.

FIG. 9 is a flowchart of a computer-implemented method for implementing a VC that assists patients in speaking, which may be implemented using the system shown in FIG. 1.

DETAILED DESCRIPTION

Figure 1:
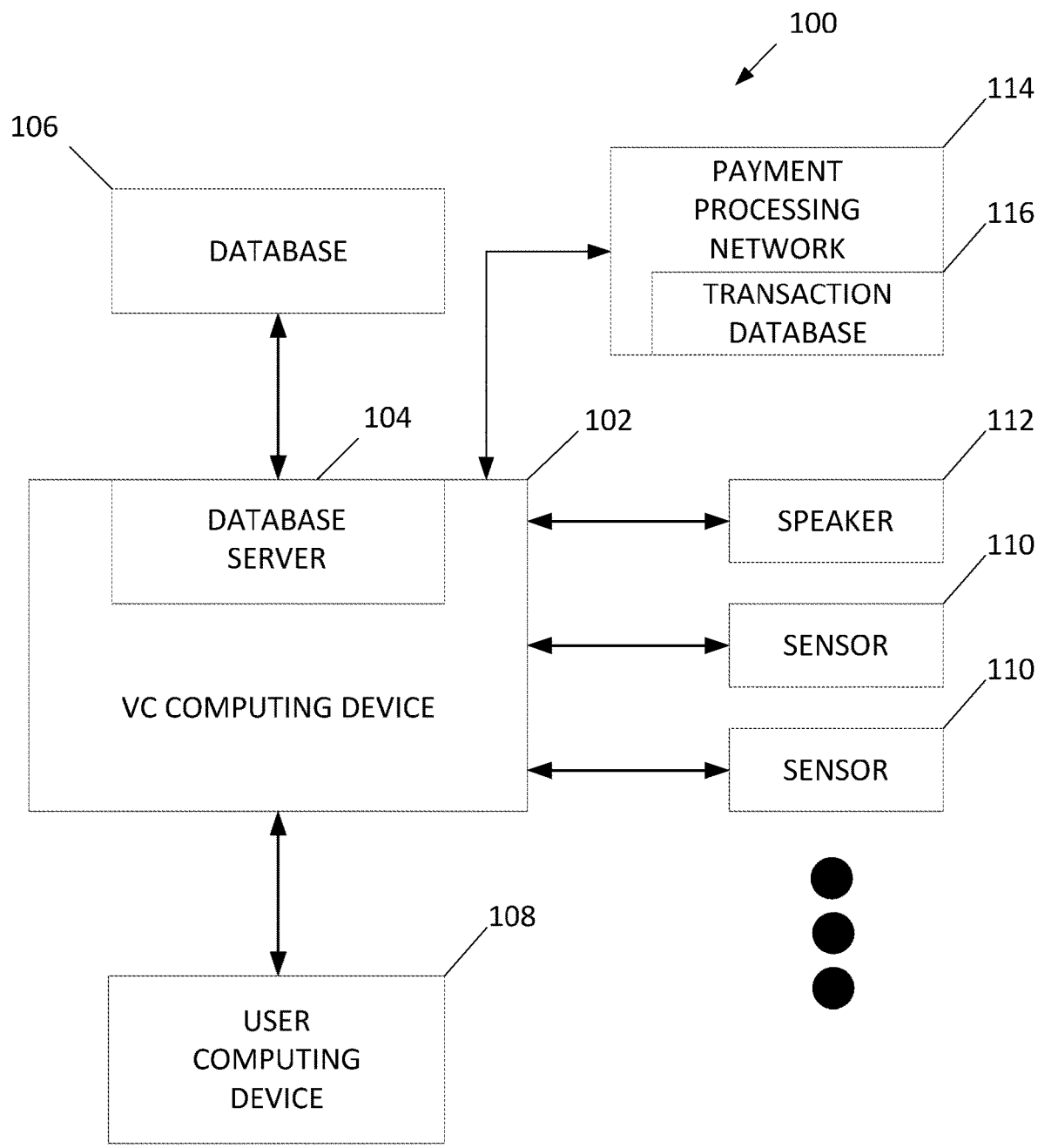
FIGS. 1-9 show example embodiments of the methods and systems described herein.

The following detailed description illustrates embodiments of the disclosure by way of example and not by way of limitation. The description enables one skilled in the art to make and use the disclosure, describes several embodiments, adaptations, variations, alternatives, and uses of the disclosure, including what is presently believed to be the best mode of carrying out the disclosure. The disclosure is described as applied to an example embodiment, namely, systems and methods utilizing a virtual caregiver (VC) computing device. The VC computing device may be in communication with, for example, a database, one or more user computing devices, one or more sensors, one or more loudspeakers, a payment processing network, and/or other devices (e.g., wearable smart devices, smart watches, mobile phones, tablets, etc.).

The VC computing device may generate and keep track of tasks that are supposed to be performed by an individual, such as individual requiring care. The tasks tracked by the VC computing device may include, for example, taking medication, bathing, performing household chores, going to doctors, going to get a haircut, purchasing food, going out to lunch, and other tasks that some patients may have difficulty remembering. As used herein, "patient" or user or senior user may refer to individuals requiring care from a caregiver. The patient, user or senior user need not be physically located in a hospital, rather, the patient, user or senior user may be in a nursing home or assisted living facility. In addition, the patient, user or senior user may also be in their own home taking care of themselves with assistance from caregivers.

The VC computing device may generate the tasks based on received data indicating that an activity must be performed (sometimes referred to herein as "task data"). The task data may include, for example, data received via manual input at a user computing device (e.g., via a mobile "app"), audio data (e.g., speech) indicating that the activity should be performed (e.g., a verbal reminder given by a caregiver and received by a voice-controlled computing device), and/or reminders included in electronic messages (e.g., email or short messaging service (SMS) messages). The VC computing device may store the generated tasks in a task database, and collect sensor data and/or transaction data to determine whether the tasks have been completed. For example, a microphone may be used to detect audio data indicating that a medication has been taken (e.g., a sound of a pill bottle being opened and a pill being swallowed). Likewise, the VC computing device may retrieve transaction data from a payment network corresponding to a grocery purchase, indicating that the patient has remembered to purchase food. The grocery purchase may be made by the patient or by a caregiver on behalf of the patient. Based on the determination, the VC computing device may record tasks in the task database as complete or incomplete, and may generate alerts based on the record (e.g., displaying an alert to the caregiver via the mobile app).

In some embodiments, VC computing device may be additionally configured to assist patients (e.g., dementia patients) in recalling words and ideas when speaking. For example, the VC computing device may record, using the sensors (e.g., a microphone), past instances of speech (e.g., stories, remarks, questions, and/or other utterances) of the patient, and identify the past instance of speech as corresponding to a current instance of speech of the patient. If the patient has difficulty with the current instance of speech (e.g., struggling to find a word), the VC computing device may generate an audio reminder to assist the patient in remembering the intended speech and/or assist others in understanding the patient. In other words, the patient may tell a story that is received by a remote microphone, transcribed, and cataloged by the VC computing device in a memory device. Then, later when the patient is repeating the story but struggles to remember the details, the cataloged details of the story may be retrieved by the VC computing device and may be provided to the patient (e.g., an audio reminder) to help them remember the story.

The VC computing device includes a processor in communication with a memory. The VC computing device may be in communication with at least one database for storing information, such as, for example, task data (e.g., data corresponding to user tasks tracked by the VC computing device), sensor data, transaction data, and/or speech data, as described below.

The VC computing device may further be in communication with one or more sensors (e.g., microphones), speakers, and/or other remote devices (wearable smart devices, smart watches, mobile phones, tablets, etc.). For example, in some embodiments, the VC computing device may be in communication with a "smart speaker" including a microphone that receives an audio input (e.g., speech commands) and a speaker through which the smart speaker may respond to speech commands (e.g., providing information, playing music, and/or other audio responses). For example, AMAZON ECHO or ALEXA devices may be used.

The VC computing device may further be in communication with a payment processing network, from which the VC computing device may retrieve transaction data corresponding to purchases (e.g., using a payment card or payment account) made by the patient. In some embodiments, the VC computing device may be capable of monitoring transactions made via the payment processing network in real time. In some embodiments, the payment processing network may include a transaction database that stores transaction data, and the VC computing device may retrieve the stored transaction data from the transaction database. As described below, the VC computing device may use such transaction data to determine whether the patient has completed tasks when those tasks include making a purchase.

In the example embodiment, the VC computing device may be configured to receive task data. In some embodiments, the task data may be received from a user device (e.g., a wearable smart device, a personal computer (PC), tablet computer, or mobile telephone). For example, the user device may be associated with a caregiver, and the caregiver may enter tasks to be completed by a patient at the user device via a user interface (e.g., a mobile "app" and/or web page) provided by the VC computing device. The user interface may enable the caregiver, for example, to enter a particular activity that must be performed by the patient (e.g., taking a medication, bathing, paying a bill, and/or other such activities) and a corresponding due date. Such task data may be used to generate tasks (e.g., a specific data element that includes the activity to be completed and associated data), as described below.

The VC computing device will be trained to detect sounds and identify tasks being completed. For example, if the patient must take medication at noon every day, the system will be trained to identify the sounds associated with completing that task (the pills rattling in the bottle, the cap being removed, etc.).

In some embodiments, the task data may be received from a sensor (e.g., a microphone, camera, wearable smart device, smart medicine cabinet, etc.). For example, in embodiments wherein the VC computing device is in communication with a smart speaker, the VC computing device may receive direct commands via the smart speaker to create tasks, for example, from the caregiver. Additionally or alternatively, the smart speaker may detect audio data (e.g., speech data) indicating that a task should be performed (e.g., the caregiver giving verbal instructions to the patient) and transmit the audio data to the VC computing device. The VC computing device may generate tasks based on such audio data, for example, utilizing artificial intelligence (AI) and/or machine learning techniques. To train the system using machine learning, sample audio data of a sound to be recognized (such as the sound of a pill bottle being opened) are provided to the machine learning model. Several examples are used that contain the sound, as well as samples that do not contain the sound to allow the model to teach the model to differentiate and identify the identified sound. Other sounds of interest could include the sound of a faucet filling a glass of water, the sound of a microwave chime, or a refrigerator door opening or closing. Based on the sound identification, the VC computing device may create a corresponding follow up task such as placing a future order for groceries or picking up a medication.

The VC computing device may be further configured to generate, based on the task data, a task including a task identifier, a fulfillment condition (e.g., the specific activity to be performed), and a time deadline. The VC computing device may generate the task identifier, and identify the fulfillment condition and the time deadline based on the received task data. For example, the fulfillment condition and time deadline may be entered manually via the user interface, as described above. Additionally or alternatively, the fulfillment condition and time deadline may be identified from audio data utilizing, for example, AI and/or machine learning techniques, as described above. In order to determine that a specific task has been completed, sample audio of an event signaling completion will be provided to the machine learning model and further trained with sounds that do not contain the audio of the event to train the system to recognize the audio signaling completion of the event.

The VC computing device may be further configured to store the generated task in a task database. For example, the VC computing device may store each generated task identifier in the task database and store the corresponding fulfillment condition, time deadline, and/or other data in association with the task identifier.

The VC computing device may be further configured to receive sensor data from one or more sensors. The sensors may include for example, the microphone and/or smart speaker. In some embodiments, the sensors may include "smart" pill bottles or containers capable of detecting opening and closing of the pill container and/or removal of pills from the container. In some embodiments, the sensors may include smart appliances that are capable of communicating data to the VC computing device. For example, a smart refrigerator may detect when contents (e.g., groceries) are added to or removed from the refrigerator (e.g., using a door sensor, camera, or other sensor), and a smart washing machine may detect when laundry is being cleaned.

The VC computing device may further be configured to retrieve transaction data. For example, in some embodiments, the VC computing device may parse transaction data associated with a purchase which is transmitted via the payment processing network for transaction data relevant to determining whether a fulfillment condition has occurred. In such embodiments, the VC computing device may track usage of a payment card account or other bank account associated with the patient. Additionally or alternatively, in some embodiments, the VC computing device may generate and perform a query to retrieve relevant transaction data from the transaction database. In some such embodiments, the VC computing device may generate the query using AI and/or machine learning techniques. For example, data may be provided to the machine learning model that can be tied to a specific task by the vendor involved. The model may be trained to recognize a particular vendor and recognized that the patient has completed a task. Using the retrieved transaction data, the VC computing device may be able to determine that the patient has remembered to, for example, pay a bill, purchase food, purchase a medication, attend a doctor visit, or performed other activities that may be associated with a payment transaction.

The VC computing device may be further configured to compare the received sensor data and/or transaction data to the fulfillment conditions stored in the task database to determine that the fulfillment condition has been performed. For example, the VC computing device may periodically parse through each of the fulfillment conditions to determine, based on the received sensor data and/or transaction data, whether the fulfillment condition has been met. In some embodiments, the VC computing device may utilize AI and/or machine learning techniques to process the sensor data and/or transaction data so that the sensor data may be used to make such a determination. For example, the VC computing device may identify a certain audio signal (e.g., a sound) as an indicator that the patient is taking and/or has taken a certain medication. The task may be to take a particular medication at noon. The fulfillment condition may be verified by the VC computing device by detecting the sound of the cabinet being open, the pill bottle being removed and opened, and the sound of the patient taking the pill. In some examples, a sensor that is part of a smart pill bottle may indicate the pill bottle for a certain medication has been opened. In another example, transaction data may be used to confirm fulfillment of the fulfillment condition. For example, transaction data associated with paying for a haircut may be used to confirm fulfillment of that task based on an identification of the vendor. Machine learning techniques may be used to determine which bills are associated with which vendors and which tasks. For example, a bill received from vendor X may be for grass cutting services that the patient receives at their house. Payment of that bill may satisfy the condition of having the yard maintained.

The VC computing device may be further configured to record the task as fulfilled based on the determination. The VC computing device may store the record in association with the corresponding task identifier in the task database. In some embodiments, the VC computing device may parse the records and time deadlines in the task database to identify tasks that are recorded as being unfulfilled past the time deadline. For each of the identified overdue tasks, the VC computing device may generate an alert, which may be provided to, for example, the caregiver and/or the patient. For example, the VC computing device may transmit an email, SMS message, and/or another form of notification to the user computing device. Additionally or alternatively, the VC computing device may generate an audio notification (e.g., at the smart speaker) to remind the patient to perform the overdue task.

In some embodiments, VC computing device may be additionally configured to assist patients (e.g., dementia patients) in recalling words and ideas when speaking. For example, the VC computing device may record past instances of speech (e.g., stories, remarks, questions, and/or other utterances) of the patient and identify the past instance as corresponding to a current instance of speech of the patient. If the patient has difficulty with the current instance of speech (e.g., pausing unnaturally and/or struggling to find a next word), the VC computing device may generate an audio reminder to assist the patient in remembering the intended speech and/or assist others in understanding the patient. As an example, the VC computing device may record a story being told by the patient. Subsequently, the audio obtained by the VC computing device is parsed and transcribed to text. Key words may be stored in relation to the story. Later, when the patient is retelling the same story, the VC computing device may detect forgetfulness based upon an extended period of silence from the patient. Alternatively, the VC computing device may be prompted of forgetfulness by an audio prompt from the patient or the caregiver. The VC computing device can search based on the key words to identify the story and further provide details to the patient so that they remember the story and are able to complete telling the story.

In such embodiments, the VC computing device may detect, at the sensor, a first instance of speech (e.g., the past instance of speech). For example, in embodiments where the VC computing device is in communication with a microphone and/or smart speaker, the VC computing device may record speech made by the patient. The VC computing device may store the detected first instance of speech in a database (e.g., a speech database).

In such embodiments, the VC computing device may detect, at the sensor (e.g., the microphone and/or smart speaker), a second instance of speech (e.g., the current instance of speech), and in response to the detection, compare the second instance of speech to the first instance of speech. The VC computing device may determine that the second instance of speech corresponds to the first instance of speech (e.g., they correspond to the same story) and generate, at a loudspeaker (e.g., a loudspeaker included in the smart speaker), an audio reminder. The audio reminder may include, for example, key words or phrases from the first instance of speech that may assist the patient and/or other listeners in recalling the intended speech. In some embodiments, the VC computing device may utilize AI and/or machine learning techniques, for example, to determine that the second instance of speech corresponds to the first instance of speech and/or to generate the audio reminder.

The technical problems addressed by the disclosure include at least one of: (i) inefficiency in automating the tracking tasks that must be performed by an individual requiring care; (ii) inability of computing devices to automatically generate tasks based on received speech; (iii) inability of computing devices to determine that a task has been performed remotely; (iv) inability of computing devices to generate automatic alerts for a remote caregiver that a task has been performed; and/or (v) inability of a computing device to determine that a task has been completed based on transaction data corresponding to payment transactions.

The technical effects achieved by the systems and methods described herein include at least one of: (i) receiving task data from a patient or caregiver; (ii) automatically generating, based on the task data, a task including a task identifier, a fulfillment condition (e.g., what needs to be done to complete the task), and a time deadline; (iii) storing the generated task in a task database along with the task identifier, the fulfillment condition and the time deadline; (iv) receiving, from at least one sensor, sensor data; (v) retrieving, from a payment processing network, transaction data; (vi) comparing at least one of the received sensor data and the retrieved transaction data to the fulfillment condition to determine that the fulfillment condition has occurred; and/or (vii) record, in the task database, the task as fulfilled based on the determination that the fulfillment condition has occurred. In the example embodiment, sensor data may be used to confirm fulfillment without the use of transaction data. In another embodiment, the sensor data and the transaction data can be used in combination together to confirm fulfillment of the task. For example, buying groceries may be detected using transaction data received by the payment processor, loading the groceries in a smart refrigeration (Internet of Things (IoT) device) and/or smart cabinets may be detected by sensors, and eating the groceries by the patient may be detected using microphone/cameras or other sensors.

The resulting technical benefits achieved by the systems and methods of the disclosure include at least one of: (i) increased efficiency in tracking tasks that must be performed by an individual requiring care; (ii) ability for computing devices to automatically generate tasks based on received speech; (iii) inability for computing devices to determine that a task has been performed remotely; (iv) ability for computing devices to generate automatic alerts for a remote caregiver that a task has been performed, (v) ability for a computing device to determine that a task has been completed based on transaction data corresponding to payment transactions.

In one embodiment, a computer program is provided, and the program is embodied on a computer readable medium. In an example embodiment, the system is executed on a single computer system, without requiring a connection to a server computer. In a further example embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). In a further embodiment, the system is run on an iOS® environment (iOS is a registered trademark of Cisco Systems, Inc. located in San Jose, CA). In yet a further embodiment, the system is run on a Mac OS® environment (Mac OS is a registered trademark of Apple Inc. located in Cupertino, CA). The application is flexible and designed to run in various different environments without compromising any major functionality. In some embodiments, the system includes multiple components distributed among a plurality of computing devices. One or more components are in the form of computer-executable instructions embodied in a computer-readable medium. The systems and processes are not limited to the specific embodiments described herein. In addition, components of each system and each process can be practiced independently and separately from other components and processes described herein. Each component and process can also be used in combination with other assembly packages and processes.

In one embodiment, a computer program is provided, and the program is embodied on a computer readable medium and utilizes a Structured Query Language (SQL) with a client user interface front-end for administration and a web interface for standard user input and reports. In another embodiment, the system is web enabled and is run on a business-entity intranet. In yet another embodiment, the system is fully accessed by individuals having an authorized access outside the firewall of the business-entity through the Internet. In a further embodiment, the system is being run in a WINDOWS® environment (WINDOWS is a registered trademark of Microsoft Corporation, Redmond, Washington). The application is flexible and designed to run in various different environments without compromising any major functionality.

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

As used herein, the term "database" may refer to either a body of data, a relational database management system (RDBMS), or to both. A database may include any collection of data including hierarchical databases, relational databases, flat file databases, object-relational databases, object oriented databases, and any other structured collection of records or data that is stored in a computer system. The above examples are for example only, and thus are not intended to limit in any way the definition and/or meaning of the term database. Examples of RDBMS's include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, California; IBM is a registered trademark of International Business Machines Corporation, Armonk, New York; Microsoft is a registered trademark of Microsoft Corporation, Redmond, Washington; and Sybase is a registered trademark of Sybase, Dublin, California).

The term processor, as used herein, may refer to central processing units, microprocessors, microcontrollers, reduced instruction set circuits (RISC), application specific integrated circuits (ASIC), logic circuits, and any other circuit or processor capable of executing the functions described herein.

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are for example only, and are thus not limiting as to the types of memory usable for storage of a computer program.

As used herein, the terms "transaction card," "financial transaction card," and "payment card" refer to any suitable transaction card, such as a credit card, a debit card, a prepaid card, a charge card, a membership card, a promotional card, a frequent flyer card, an identification card, a gift card, and/or any other device that may hold payment account information, such as mobile phones, Smartphones, personal digital assistants (PDAs), key fobs, and/or computers. Each type of transactions card can be used as a method of payment for performing a transaction.

Figure 2:
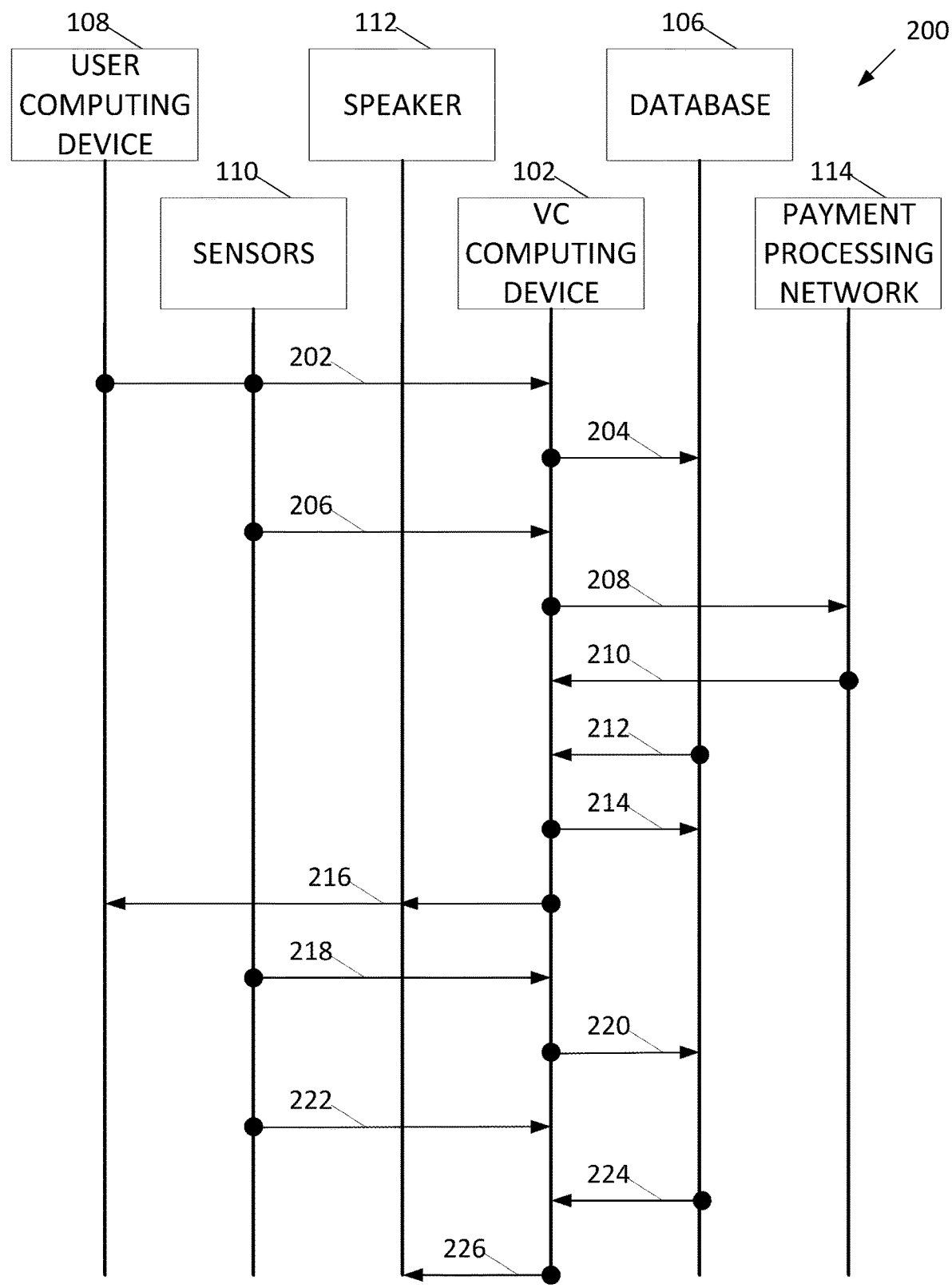

FIG. 1 is a simplified block diagram of an exemplary virtual caregiver (VC) system 100 in accordance with one example embodiment of the present disclosure. FIG. 2 is a data flow diagram of an exemplary data flow 200 within VC system 100. VC system 100 includes a VC computing device 102 that includes at least one database server 104. VC system 100 may further include one or more user computing devices 108 (e.g., a PC, tablet computer, and/or mobile telephone), sensors 110 (e.g., microphones), speakers 112, and/or payment processing network 114.

VC computing device 102 may include a processor in communication with a memory. VC computing device 102 may be in communication with database 106 via database server 104.

VC computing device 102 may further be in communication with one or more sensors 110, speakers 112, and/or other remote devices (e.g., microphones, cameras, IoT devices, wearables, other computing or smart devices, etc.). For example, in some embodiments, VC computing device 102 may be in communication with a "smart speaker" including a microphone that receives an audio input (e.g., speech commands) and speaker 112 through which the smart speaker may respond to speech commands (e.g., providing information, playing music, and/or other audio responses).

VC computing device 102 may further be in communication with payment processing network 114, from which VC computing device 102 may retrieve transaction data corresponding to purchases (e.g., using a payment card) made by the patient. In some embodiments, VC computing device 102 may be capable of monitoring transactions made via payment processing network 114 in real time. In some embodiments, payment processing network 114 may include a transaction database 116 that stores transaction data, and VC computing device 102 may retrieve the stored transaction data from transaction database 116. As described below, VC computing device 102 may use such transaction data to determine whether the patient has completed tasks. For example, payment processing network 114 may include an electronic transaction payment card processing system, such as a payment card processing system using the Mastercard® interchange network (Mastercard is a registered trademark of Mastercard International Incorporated located in Purchase, N.Y.). The Mastercard® interchange network is a proprietary communications standard promulgated by Mastercard International Incorporated® for the exchange of electronic transaction data between financial institutions that have registered with Mastercard International Incorporated®. For example, the messages sent over the payment processing network may include an ISO 8583 computer message.

In the example embodiment, VC computing device 102 may be configured to receive task data 202. In some embodiments, task data 202 may be received from user computing device 108. For example, user computing device 108 may be associated with a caregiver, and the caregiver may enter tasks to be completed by a patient at user computing device 108 via a user interface (e.g., a mobile "app" and/or web page) provided by VC computing device 102. The user interface may enable the caregiver, for example, to enter a particular activity that must be performed by the patient (e.g., taking a medication, bathing, paying a bill, and/or other such activities) and a corresponding due date. Such task data 202 may be used to generate tasks 204 (e.g., a specific data element that includes the activity to be completed and associated data), as described below.

In some embodiments, task data 202 may additionally or alternatively be received from one or more sensors 110. For example, in embodiments wherein VC computing device 102 is in communication with a smart speaker, VC computing device 102 may receive direct commands via the smart speaker to create tasks 204, for example, from the caregiver. Additionally or alternatively, the smart speaker may detect audio data (e.g., speech data) indicating that an activity should be performed (e.g., the caregiver giving verbal instructions to the patient) and transmit the audio data to VC computing device 102. VC computing device 102 may generate tasks 204 based on such audio data, for example, utilizing artificial intelligence (AI) and/or machine learning techniques.

VC computing device 102 may be further configured to generate, based on task data 202, tasks 204 that include a task identifier, a fulfillment condition (e.g., the specific activity to be performed), and a time deadline. VC computing device 102 may generate the task identifier and identify the fulfillment condition and the time deadline based on the received task data 202. For example, the fulfillment condition and time deadline may be entered manually via the user interface, as described above. Additionally or alternatively, the fulfillment condition and time deadline may be identified from audio data utilizing, for example, AI and/or machine learning techniques, as described above.

VC computing device 102 may be further configured to store the generated task 204 in database 106 (e.g., in a task database). For example, VC computing device 102 may store each generated task identifier in database 106 and store the corresponding fulfillment condition, time deadline, and/or other data in association with the task identifier.

VC computing device 102 may be further configured to receive sensor data 206 from sensors 110. Sensors 110 may include, for example, the microphone and/or smart speaker. In some embodiments, sensors 110 may include "smart" pill bottles or containers capable of detecting opening and closing of the pill container and/or removal of pills from the container. In some embodiments, sensors 110 may include smart appliances or other IoT devices that are capable of communicating data to VC computing device 102. For example, a smart refrigerator may detect when contents (e.g., groceries) are added to or removed from the refrigerator (e.g., using a door sensor, camera, or other sensor), and a smart washing machine may detect when laundry is being cleaned.

VC computing device 102 may further be configured to retrieve transaction data 210 from payment processing network 114. For example, in some embodiments, VC computing device 102 may parse transaction data 210 transmitted via payment processing network 114 for transaction data 210 relevant to determining whether a fulfillment condition has occurred. In such embodiments, VC computing device 102 may track usage of a payment card account or other bank account associated with the patient. Additionally or alternatively, in some embodiments, VC computing device 102 may generate and perform a query 208 to retrieve relevant transaction data 210 from transaction database 116. In some such embodiments, VC computing device 102 may generate the query using AI and/or machine learning techniques. Using the retrieved transaction data 210, VC computing device 102 may be able to determine that the patient has remembered to, for example, pay a bill, purchase food, purchase a medication, attend a doctor visit, or performed other activities that may be associated with a payment transaction.

VC computing device 102 may be further configured to compare 212 the received sensor data 206 and/or transaction data 210 to the fulfillment conditions stored in database 106 to determine that the fulfillment condition has been performed. For example, VC computing device 102 may periodically parse through each of the fulfillment conditions of the stored tasks 204 to determine, based on the received sensor data 206 and/or transaction data 210, whether the fulfillment condition has been met. In some embodiments, VC computing device 102 may utilize AI and/or machine learning techniques to process sensor data 206 and/or transaction data 210 so that the sensor data may be used to make such a determination. For example, VC computing device 102 may identify a certain audio signal (e.g., a sound) as an indicator that the patient is taking and/or has taken a certain medication.

VC computing device 102 may be further configured to record 214 the task as fulfilled (or unfulfilled) based on the determination. VC computing device 102 may store record 214 in association with the corresponding task identifier in database 106. In some embodiments, VC computing device 102 may parse records 214 and the time deadlines in database 106 to identify tasks 204 that are recorded as being unfulfilled past the time deadline. For each of the identified overdue tasks 204, VC computing device 102 may generate an alert 216, which may be provided to, for example, the caregiver and/or the patient. For example, VC computing device 102 may transmit an email, SMS message, and/or another form of notification to user computing device 108. Additionally or alternatively, VC computing device 102 may generate an audio notification (e.g., at the smart speaker) to remind the patient to perform the overdue task.

In some embodiments, VC computing device may be additionally configured to assist patients (e.g., dementia patients) in recalling words and ideas when speaking. For example, VC computing device 102 may record past instances of speech (e.g., stories, remarks, questions, and/or other utterances) of the patient using sensors 110 and identify the past instance as corresponding to a current instance of speech of the patient. If the patient has difficulty with the current instance of speech (e.g., pausing unnaturally and/or struggling to find a next word), VC computing device 102 may generate an audio reminder (e.g., using speaker 112) to assist the patient in remembering the intended speech and/or assist others in understanding the patient.

In such embodiments, VC computing device 102 may detect, at sensor 110, a first instance of speech 218 (e.g., the past instance of speech). For example, in embodiments where VC computing device 102 is in communication with a microphone and/or smart speaker, VC computing device 102 may record speech made by the patient. VC computing device 102 may store speech data 220 derived from the detected first instance of speech 218 in database 106 (e.g., in a speech database).

In such embodiments, VC computing device 102 may detect, at sensor 110 (e.g., the microphone and/or smart speaker), a second instance of speech 222 (e.g., the current instance of speech), and in response to the detection, compare 224 second instance of speech 228 to first instance of speech 218. VC computing device 102 may determine that second instance of speech 222 corresponds to first instance of speech 218 (e.g., they correspond to the same story) and generate, at speaker 112, an audio reminder 226. Audio reminder 226 may include, for example, key words or phrases from the first instance of speech that may assist the patient and/or other listeners in recalling the intended speech. In some embodiments, VC computing device 102 may utilize AI and/or machine learning techniques, for example, to determine that second instance of speech 222 corresponds to first instance of speech 218 and/or to generate the audio reminder 226.

Figure 3:
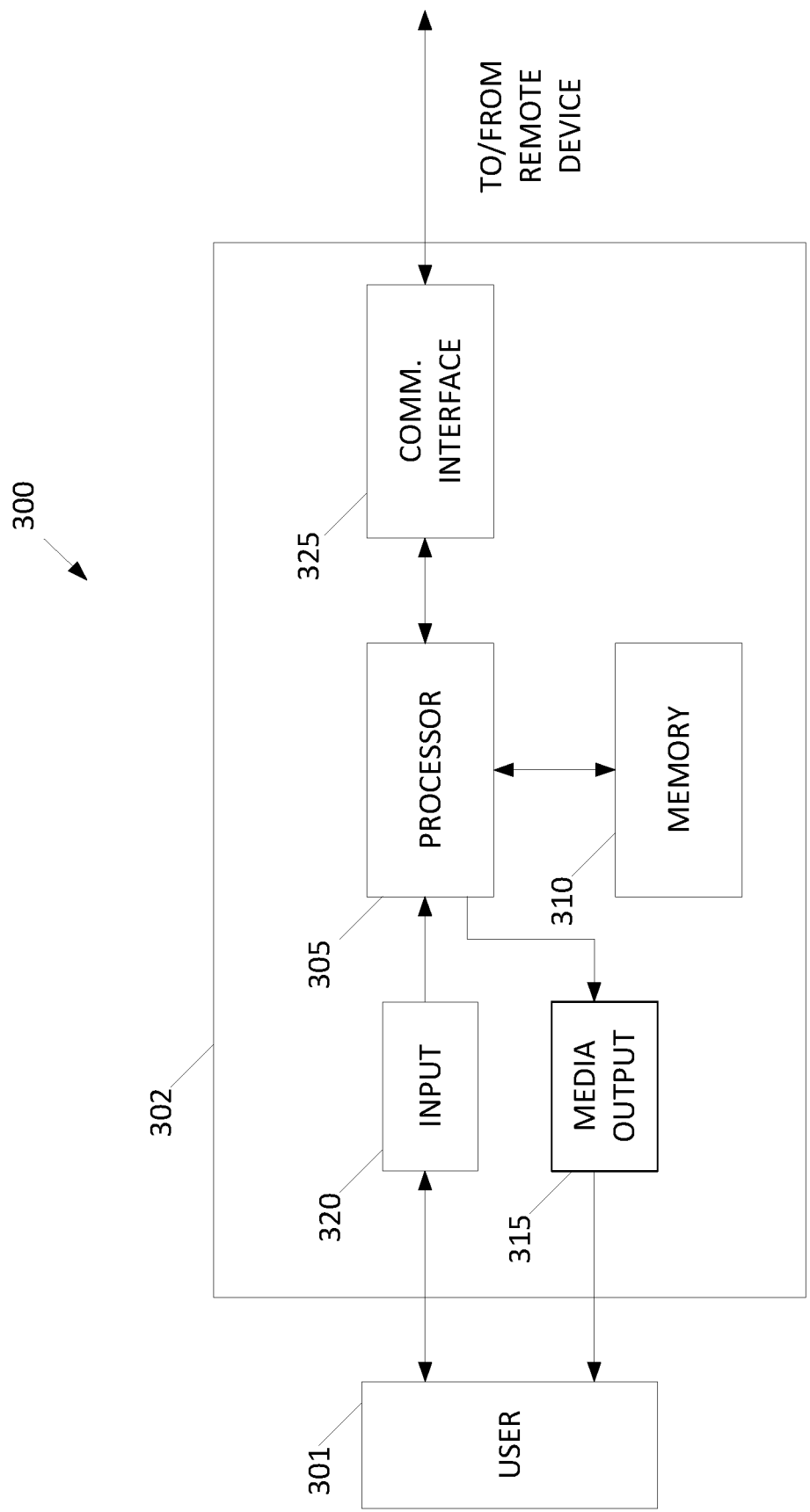

FIG. 3 illustrates an example configuration of a client system 300 in accordance with one embodiment of the present disclosure. In the example embodiment, client system 300 includes at least one user computing device 302, operated by a user 301. User computer device 302 may include, but is not limited to, one or more of VC computing device 102, user computing device 108, sensors 110, and/or speakers 112 (all shown in FIG. 1). User computer device 302 includes a processor 305 for executing instructions, and a memory area 310. In some embodiments, executable instructions are stored in memory area 310. Processor 305 may, for example, include one or more processing units (e.g., in a multi-core configuration). Memory area 310 may, for example, be any device allowing information such as executable instructions and/or transaction data to be stored and retrieved. Memory area 310 may further include one or more computer readable media.

In the example embodiment, user computer device 302 further includes at least one media output component 315 for presenting information to user 301. Media output component 315 may, for example, be any component capable of converting and conveying electronic information to user 301. For example, media output component 315 may be a display component configured to display component life-cycle data in the form of reports, dashboards, communications, and the like In some embodiments, media output component 315 includes an output adapter (not shown), such as a video adapter and/or an audio adapter, which is operatively coupled to processor 305 and operatively connectable to an output device (also not shown), such as a display device (e.g., a cathode ray tube (CRT), liquid crystal display (LCD), light emitting diode (LED) display, or "electronic ink" display) or an audio output device (e.g., a speaker or headphones).

In some embodiments, media output component 315 is configured to include and present a graphical user interface (not shown), such as a web browser and/or a client application, to user 301. The graphical user interface may include, for example, an online store interface for viewing and/or purchasing items, and/or a wallet application for managing payment information. In some embodiments, user computer device 302 includes an input device 320 for receiving input from user 301. User 301 may use input device 320 to, without limitation, select and/or enter one or more items to purchase and/or a purchase request, or to access credential information, and/or payment information. Input device 320 may include, for example, a keyboard, a pointing device, a mouse, a stylus, a touch sensitive panel, a touch pad, a touch screen, a gyroscope, an accelerometer, a position detector, an audio input device, a fingerprint reader/scanner, a palm print reader/scanner, an iris reader/scanner, a retina reader/scanner, a profile scanner, or the like. A single component such as a touch screen may function as both an output device of media output component 315 and input device 320. User computing device 302 may also include a communication interface 325, which is communicatively connectable to a remote device such as VC computing device 102 (shown in FIG. 1). Communication interface 325 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 310 are, for example, computer readable instructions for providing a user interface to user 301 via media output component 315 and, optionally, receiving and processing input from input device 320. A user interface may include, among other possibilities, a web browser, and client application. Web browsers enable users, such as user 301, to display and interact with media and other information typically embedded on a web page or a website from a server system. A client application allows user 301 to interact with a server application from the server system. For example, instructions may be stored by a cloud service, and the output of the execution of the instructions sent to the media output component 315.

Figure 6:
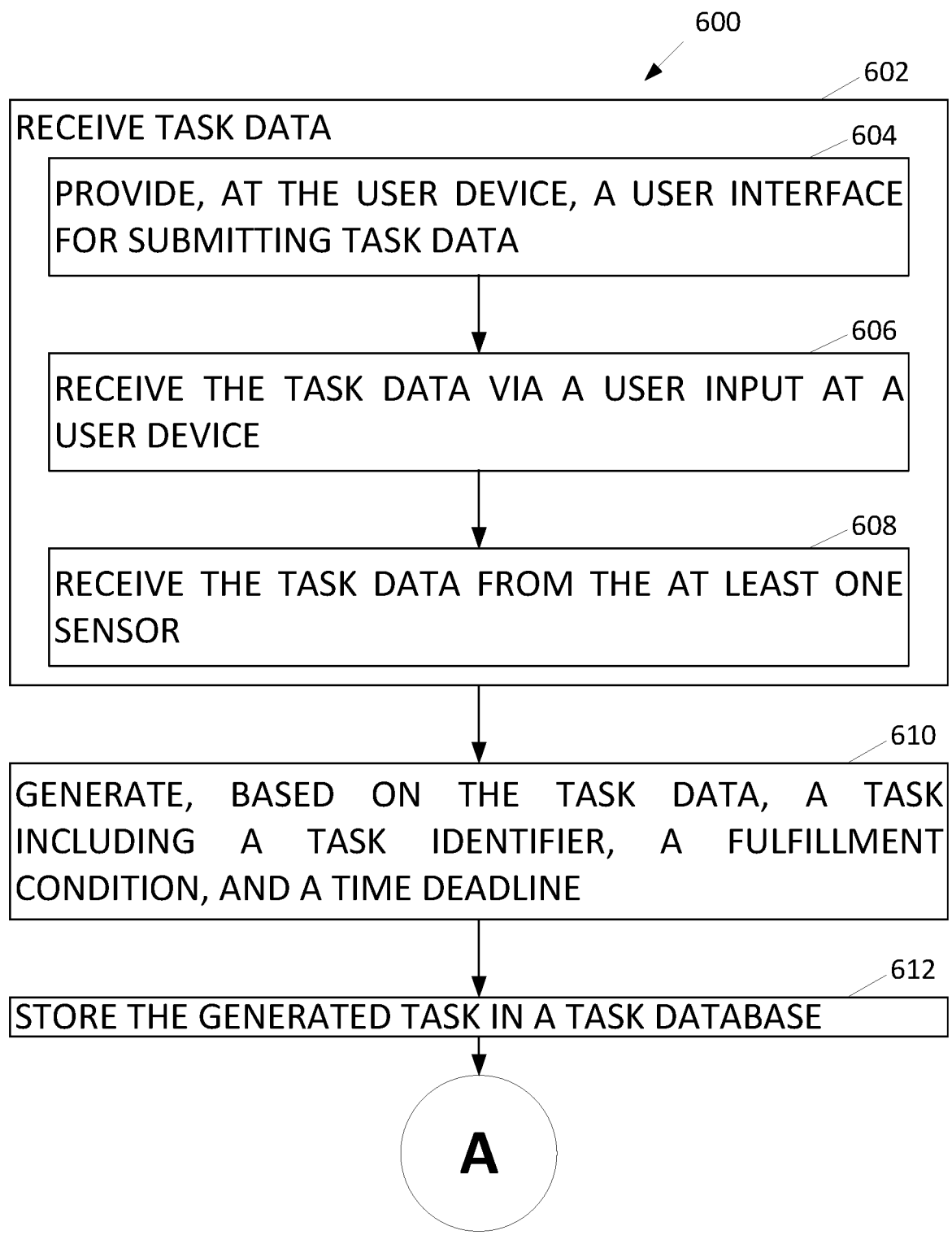
Figure 7:
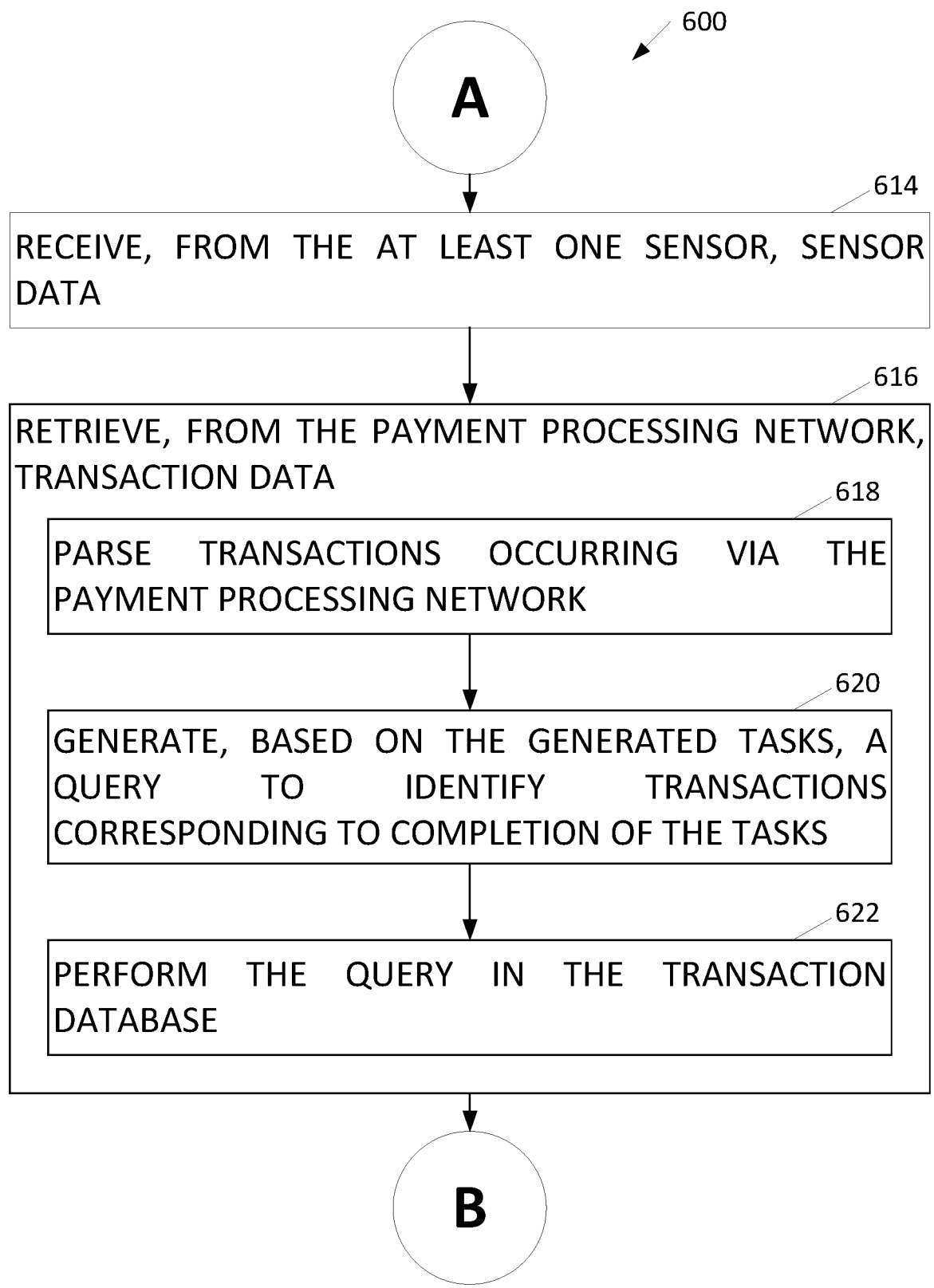
Figure 8:
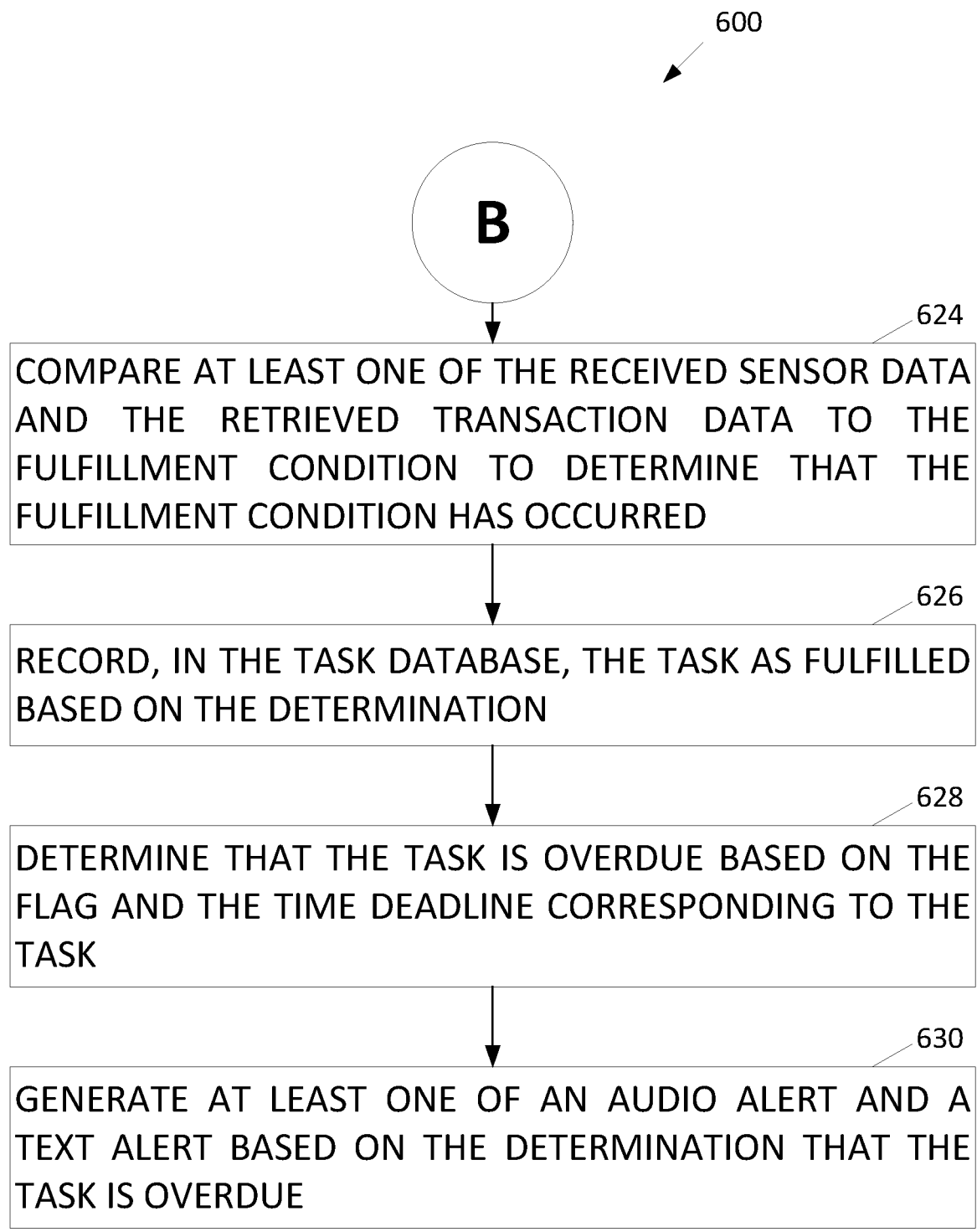

Processor 305 executes computer-executable instructions for implementing aspects of the disclosure. In some embodiments, the processor 305 is transformed into a special purpose microprocessor by executing computer-executable instructions or by otherwise being programmed. For example, the processor 305 may be programmed with instructions such that it may execute the processes as illustrated in FIGS. 6-8, below.

Figure 4:
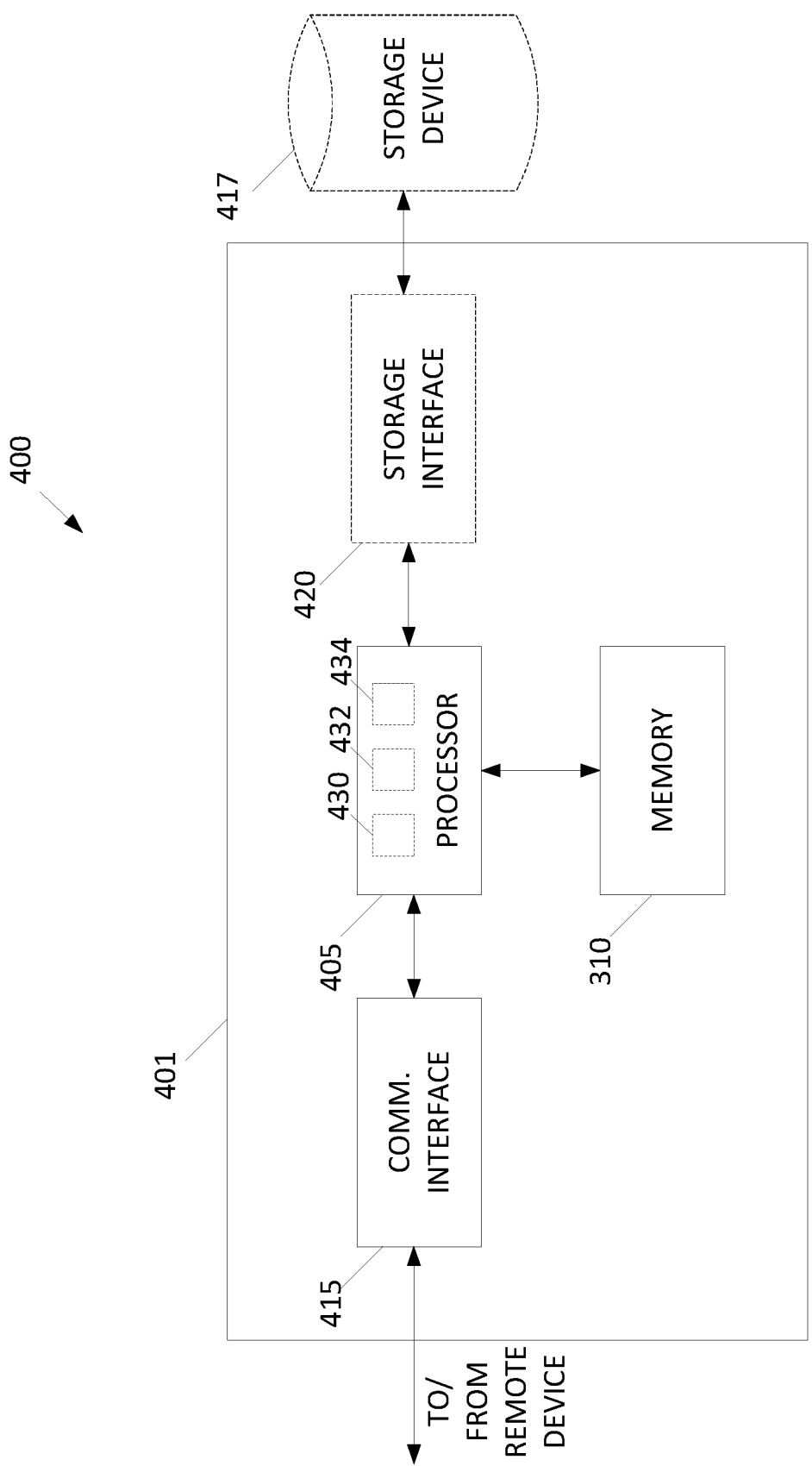

FIG. 4 illustrates an example configuration of a server system 400, such as VC computing device 102 (shown in FIG. 1). In the example embodiment, server system 400 includes at least one server computing device 401, in electronic communication with at least one storage device 417. Server computing device 401 may include, but is not limited to, VC computing device 102. In the exemplary embodiment, server computing device 401 includes a processor 405 for executing instructions (not shown) stored in a memory area 410. In an embodiment, processor 405 may include one or more processing units (e.g., in a multi-core configuration) for executing instructions. The instructions may be executed within various different operating systems on the server system 400, such as UNIX®, LINUX® (LINUX is a registered trademark of Linus Torvalds), Microsoft Windows®, etc. More specifically, the instructions may cause various data manipulations on data stored in storage device 417 (e.g., create, read, update, and delete procedures. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or other suitable programming languages, etc.).

In the example embodiment, processor 405 is operatively coupled to a communication interface 415 such that server system 400 is capable of communicating with a remote device such as a user system or another server system 400. For example, communication interface 415 may receive requests from client system 300 (FIG. 3) via the Internet, within the scope of the embodiment illustrated in FIG. 4.

In the example embodiment, processor 405 is also operatively coupled to a storage device 417, which may be, for example, any computer-operated hardware unit suitable for storing and/or retrieving data. In some embodiments, storage device 417 is integrated in server system 400. For example, server system 400 may include one or more hard disk drives as storage device 417. In certain embodiments, storage device 417 is external to server system 400 and is similar to database 106 (shown in FIG. 1). For example, server system 400 may include one or more hard disk drives as storage device 417. In other embodiments, storage device 417 is external to server system 400 and may be accessed by a plurality of server systems 400. For example, storage device 417 may include multiple storage units such as hard disks or solid state disks in a redundant array of inexpensive disks (RAID) configuration. storage device 417 may include a storage area network (SAN) and/or a network attached storage (NAS) system.

In some embodiments, processor 405 is operatively coupled to storage device 417 via a storage interface 420. Storage interface 420 may include, for example, a component capable of providing processor 405 with access to storage device 417. In an exemplary embodiment, storage interface 420 further includes one or more of an Advanced Technology Attachment (ATA) adapter, a Serial ATA (SATA) adapter, a Small Computer System Interface (SCSI) adapter, a RAID controller, a SAN adapter, a network adapter, and/or any similarly capable component providing processor 405 with access to storage device 417.

In some embodiments, processor 405 includes one or more modules for performing specific tasks executed by processor 405. For example, processor 405 may include a communication module 430, an analytics module 432, and a data management module 434.

In some embodiments, communication module 430 may be configured for, for example, receiving task data; providing, at the user device, a user interface; receiving task data may include receiving the task data via a user input at a user device; receiving the task data from the at least one sensor; receiving, from the at least one sensor, sensor data; generating at least one of an audio alert and a text alert based on the determination that the task is overdue; detecting, at the sensor, a first instance of speech; detecting, at the sensor, a second instance of speech; and/or generating an audio reminder based on the comparison.

In some embodiments, analytics module 432 may be configured for, for example, generating, based on the task data, a task including a task identifier, a fulfillment condition, and a time deadline; comparing at least one of the received sensor data and the retrieved transaction data to the fulfillment condition to determine that the fulfillment condition has occurred; determining that the task is overdue based on the record and the time deadline corresponding to the task; comparing the second instance of speech to the first instance of speech in response to the detection of the second instance of speech; and/or generating, based on the generated tasks, a query to identify transactions corresponding to completion of the tasks.

In some embodiments, data management module 434 may be configured for, for example, storing the generated task in a task database; recording, in the task database, the task as fulfilled based on the determination; storing the detected first instance of speech in a speech database; retrieving, from the payment processing network, transaction data; parsing transactions occurring via the payment processing network; and/or performing the query in the transaction database.

Memory area 410 may include, but is not limited to, random-access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), and magneto-resistive random-access memory (MRAM). The above memory types are for example only, and are thus not limiting as to the types of memory usable for storage of a computer program.

Figure 5:
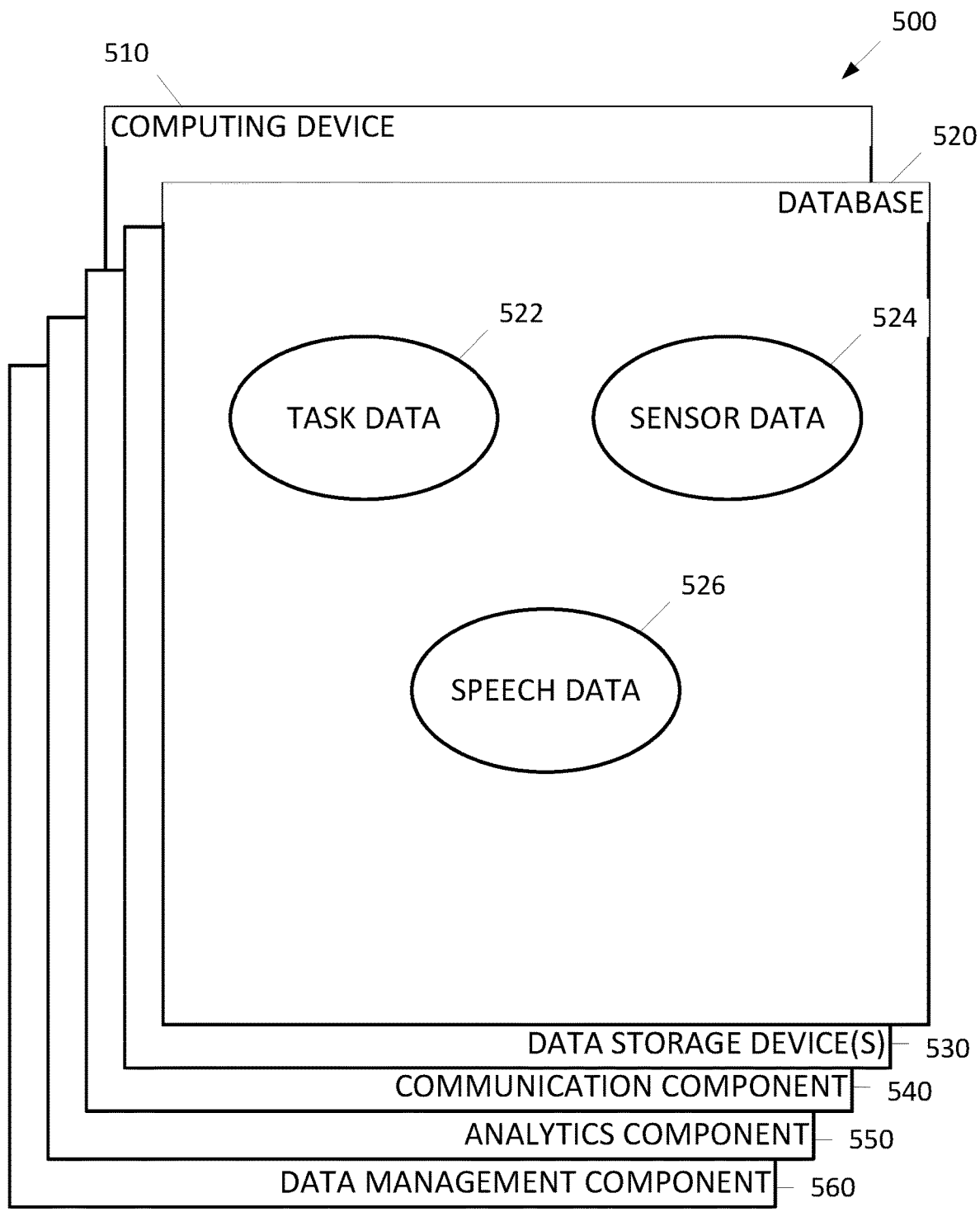

FIG. 5 is a diagram 500 of components of one or more example computing devices 510 that may be used in VC system 100 shown in FIG. 1. In some embodiments, computing device 510 is similar to VC computing device 102 (shown in FIG. 1). Database 520 may be coupled with several separate components within computing device 510, which perform specific tasks. In this embodiment, database 520 includes task data 522, sensor data 524, and speech data 526. In some embodiments, database 520 is similar to database 106 (shown in FIG. 1).

Computing device 510 includes database 520, as well as data storage devices 730 for storing data within database 520. Computing device 510 may also be in communication with one or more of a communication component 540, an analytics component 550, and a data management component 560.

In some embodiments, communication component 540 may be configured for, for example, receiving task data; providing, at the user device, a user interface; receiving task data may include receiving the task data via a user input at a user device; receiving the task data from the at least one sensor; receiving, from the at least one sensor, sensor data; generating at least one of an audio alert and a text alert based on the determination that the task is overdue; detecting, at the sensor, a first instance of speech; detecting, at the sensor, a second instance of speech; and/or generating an audio reminder based on the comparison.

In some embodiments, analytics component 550 may be configured for, for example, generating, based on the task data, a task including a task identifier, a fulfillment condition, and a time deadline; comparing at least one of the received sensor data and the retrieved transaction data to the fulfillment condition to determine that the fulfillment condition has occurred; determining that the task is overdue based on the record and the time deadline corresponding to the task; comparing the second instance of speech to the first instance of speech in response to the detection of the second instance of speech; and/or generating, based on the generated tasks, a query to identify transactions corresponding to completion of the tasks.

In some embodiments, data management component 560 may be configured for, for example, storing the generated task in a task database; recording, in the task database, the task as fulfilled based on the determination; storing the detected first instance of speech in a speech database; retrieving, from the payment processing network, transaction data; parsing transactions occurring via the payment processing network; and/or performing the query in the transaction database.

FIGS. 6, 7, and 8 depict a flowchart illustrating an example computer-implemented method 600 for implementing a VC that assists patients and caregivers in tracking tasks, which may be implemented using VC system 100 (shown in FIG. 1). Computer-implemented method 600 may be implemented by a computing device, for example, VC computing device 102 (shown in FIG. 1), in cooperation with VC system 100.

In the example embodiment, computer-implemented method 600 may include receiving 602 task data. In some embodiments, receiving 602 task data may be performed by VC computing device 102, for example, by executing communication module 430 (shown in FIG. 4).

In some embodiments, computer-implemented method may further include providing 604, at the user device, a user interface for submitting task data. In some such embodiments, providing 604 the user interface may be performed by VC computing device 102, for example, by executing communication module 430.

In some embodiments, computer-implemented method 600 may further include receiving 606 task data which may include receiving the task data via a user input at a user device. In some such embodiments, receiving 606 the task data may be performed by VC computing device 102, for example, by executing communication module 430.

In some embodiments, computer-implemented method 600 may further include receiving 608 the task data from the at least one sensor. In such embodiments, the task data may include audio signals corresponding to speech. In some such embodiments, receiving 608 the task data may be performed by VC computing device 102, for example, by executing communication module 430.

Computer-implemented method 600 may further include generating 610, based on the task data, a task including a task identifier, a fulfillment condition, and a time deadline. In some embodiments, generating 610 the task, the fulfillment condition and the time deadline may be performed by VC computing device 102, for example, by executing analytics module 432 (shown in FIG. 4).

Computer-implemented method 600 may further include storing 612 the generated task in a task database. In some embodiments, storing 612 the generated task may be performed by VC computing device 102, for example, by executing data management module 434 (shown in FIG. 4).

Computer-implemented method 600 may further include receiving 614, from the at least one sensor, sensor data. In some embodiments, the sensor data may include audio signals. In some embodiments, receiving 614 the sensor data may be performed by VC computing device 102, for example, by executing communication module 430.

Computer-implemented method 600 may further include retrieving 616, from the payment processing network, transaction data. In some embodiments, retrieving 616 the transaction data may be performed by VC computing device 102, for example, by executing data management module 434.

In some embodiments, computer-implemented method 600 may further include parsing 618 transactions occurring via the payment processing network. In some embodiments, parsing 618 transactions may be performed by VC computing device 102, for example, by executing data management module 434. Parsing the transaction data may include identifying the merchant involved in a particular transaction along with the transaction amount and time of the transaction. This parsed data may be used by the computing system to determine what product or service was purchased, and when it was purchased. This data may be further used to determine whether a task has been completed or at least whether a portion of the task has been completed. The transaction data may be used by itself or in combination with other sensor data to determine whether a task has been completed.

In some embodiments, computer-implemented method 600 may further include generating 620, based on the generated tasks, a query to identify transactions corresponding to completion of the tasks. In some embodiments, generating 620 the query is performed by VC computing device 102, for example, by executing analytics module 432.

In such embodiments, computer-implemented method 600 may further include performing 622 the query in the transaction database. In some embodiments, performing 622 the query may be performed by VC computing device 102, for example, by executing data management module 434.

Computer-implemented method 600 may further include comparing 624 at least one of the received sensor data and the retrieved transaction data to the fulfillment condition to determine that the fulfillment condition has occurred. In some embodiments, comparing 624 the received sensor data to the fulfillment condition may be performed by VC computing device 102, for example, by executing analytics module 432.

Computer-implemented method 600 may further include recording 626, in the task database, the task as fulfilled based on the determination that the fulfillment condition has occurred. In some embodiments, recording 626 the task may be performed by VC computing device 102, for example, by executing data management module 434.

In some embodiments, computer-implemented method 600 may further include determining 628 that the task is overdue based on the based on the fulfillment condition not having occurred by the time deadline corresponding to the task. In some such embodiments, determining 628 that the task is overdue may be performed by VC computing device 102, for example, by executing analytics module 432.

In such embodiments, computer-implemented method may further include generating 630 at least one of an audio alert and a text alert based on the determination that the task is overdue. In some embodiments, generating 630 the audio alert or the text alert may be performed by VC computing device 102, for example, by executing communication module 430.

Figure 9:
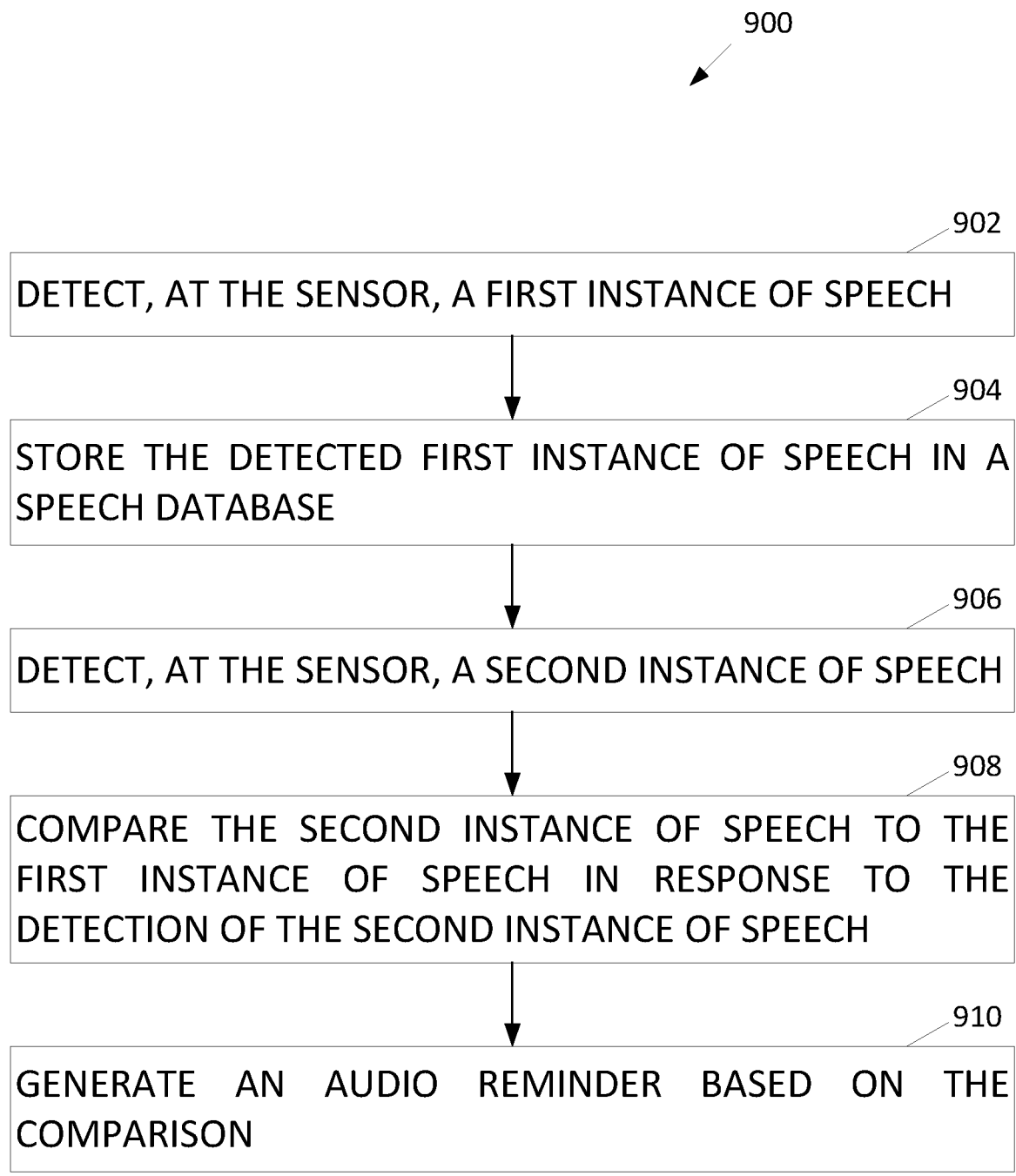

FIG. 9 depicts a flowchart illustrating an example computer-implemented method 900 for implementing a VC that assists patients in speaking, which may be implemented using VC system 100 (shown in FIG. 1). Computer-implemented method 900 may be implemented by a computing device, for example, VC computing device 102 (shown in FIG. 1), in cooperation with VC system 100.

In the exemplary embodiment, computer-implemented method 900 may include detecting 902, at the sensor, a first instance of speech. In some embodiments, detecting 902 the first instance of speech may be performed by VC computing device 102, for example, by executing communication module 430 (shown in FIG. 4).

Computer-implemented method 900 may further include storing 904 the detected first instance of speech in a speech database. In some embodiments, storing 904 the first instance of speech may be performed by VC computing device 102, for example, by executing data management module 434 (shown in FIG. 4).

Computer-implemented method 900 may further include detecting 906, at the sensor, a second instance of speech. In some embodiments, detecting 906 the second instance of speech may be performed by VC computing device 102, for example, by executing communication module 430.

Computer-implemented method 900 may further include comparing 908 the second instance of speech to the first instance of speech in response to the detection of the second instance of speech. In some embodiments, comparing 908 the second instance of speech to the first instance of speech may be performed by VC computing device 102, for example, by executing analytics module 432 (shown in FIG. 4).

Computer-implemented method 900 may further include generating 910 an audio reminder based on the comparison. In some embodiments, the audio reminder includes at least a portion of the first instance of speech. In some embodiments, generating 910 the audio reminder may be performed by VC computing device 102, for example, by executing communication module 430.

A processor or a processing element may employ artificial intelligence and/or be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based on example inputs in order to make valid and reliable predictions for novel inputs.

Additionally or alternatively, the machine learning programs may be trained by inputting sample data sets or certain data into the programs, such as image data, text data, report data, and/or numerical analysis. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, so that when subsequent novel inputs are provided the processing element may, based on the discovered rule, accurately predict the correct output. In unsupervised machine learning, the processing element may be required to find its own structure in unlabeled example inputs. In one embodiment, machine learning techniques may be used to extract data about the computer device, the user of the computer device, the computer network hosting the computer device, services executing on the computer device, and/or other data.

Based on these analyses, the processing element may learn how to identify characteristics and patterns that may then be applied to training models, analyzing transaction and authentication data, and detecting and analyzing risk.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

While the disclosure has been described in terms of various specific embodiments, those skilled in the art will recognize that the disclosure can be practiced with modification within the spirit and scope of the claims.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As will be appreciated based on the foregoing specification, the above-described embodiments of the disclosure may be implemented using computer programming or engineering techniques including computer software, firmware, hardware or any combination or subset thereof, wherein the technical effect is a system that automatically generates and tracks tasks to be performed by a patient. Any such resulting program, having computer-readable code means, may be embodied or provided within one or more computer-readable media, thereby making a computer program product, i.e., an article of manufacture, according to the discussed embodiments of the disclosure. The article of manufacture containing the computer code may be made and/or used by executing the code directly from one medium, by copying the code from one medium to another medium, or by transmitting the code over a network.

In addition, although various elements of the VC computing device are described herein as including general processing and memory devices, it should be understood that the VC computing device is a specialized computer configured to perform the steps described herein.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial locational differences from the literal language of the claims.

What is claimed is:

1. A virtual caregiver (VC) computing device comprising at least one processor in communication with at least one memory device, at least one sensor, and a payment processing network, the at least one processor configured to:
   receive task data for a selected patient;
   generate, based on the task data, at least one task to be performed by or on behalf of the patient, the task data including a task identifier, a fulfillment condition, and a time deadline;
   store the generated at least one task linked to the patient in a task database;
   receive sensor data from the at least one sensor, the sensor data relating to the task;
   retrieve transaction data from the payment processing network, the transaction data extracted from a data message transmitted over the payment processing network in response to a payment card transaction associated with a purchase made for the patient;
   compare the received sensor data and the retrieved transaction data to the fulfillment condition to determine that the fulfillment condition of the at least one task has been satisfied; and
   record, in the task database, the at least one task as fulfilled based on the determination that the fulfillment condition has been satisfied.

2. The VC computing device of claim 1, wherein the at least one processor is further configured to:
   determine that the at least one task is overdue based on the fulfillment condition not having been satisfied by the time deadline corresponding to the task; and generate at least one of an audio alert and a text alert based on the determination that the at least one task is overdue.

3. The VC computing device of claim 1, wherein to receive the task data, the at least one processor is configured to receive the task data via a user input at a user device.

4. The VC computing device of claim 3, wherein the at least one processor is further configured to provide, at the user device, a user interface for submitting task data.

5. The VC computing device of claim 1, wherein to receive the task data, the at least one processor is configured to receive the task data from the at least one sensor.

6. The VC computing device of claim 5, wherein the task data includes audio signals corresponding to speech.

7. The VC computing device of claim 1, wherein the sensor data includes audio signals.

8. The VC computing device of claim 1, wherein to retrieve the transaction data, the at least one processor is configured to retrieve transaction data processed over the payment processing network that is in communication with the at least one processor, and parse the transaction data to identify a merchant involved in the transaction and the time when the transaction occurred.

9. The VC computing device of claim 1, wherein the payment processing network includes a transaction database, and wherein to retrieve the transaction data, the at least one processor is configured to:
generate, based on the generated tasks, a query to identify transactions corresponding to completion of a particular task; and
execute the query within the transaction database.

10. The VC computing device of claim 1, wherein the at least one processor is further configured to:
detect, at the at least one sensor, a first instance of speech;
store the detected first instance of speech in a speech database;
detect, at the at least one sensor, a second instance of speech;
compare the second instance of speech to the first instance of speech in response to the detection of the second instance of speech; and
generate an audio reminder based on the comparison, the audio reminder communicated through a speaker to the patient.

11. The VC computing device of claim 10, wherein the audio reminder includes at least a portion of the first instance of speech.

12. The VC computing device of claim 1, wherein the sensor is a smart container, and wherein the sensor data includes data indicating (1) opening and closing of the smart container or (2) addition and removal of contents from the smart container.

13. The VC computing device of claim 7, wherein the fulfillment condition is associated with consuming of a product, and wherein the audio signals included in the received sensor data indicate that the product has been consumed.

14. A computer-implemented method for implementing a virtual caregiver (VC) performed by a VC computing device including at least one processor in communication with at least one memory device, at least one sensor, and a payment processing network, the computer-implemented method comprising:
receiving, by the VC computing device, task data for a selected patient;
generating, by the VC computing device, based on the task data, a task to be performed by or on behalf of the patient, the task data including a task identifier, a fulfillment condition, and a time deadline;
storing, by the VC computing device, the generated task linked to the patient in a task database;
receiving sensor data, by the VC computing device, from the at least one sensor, the sensor data relating to the task;
retrieving transaction data, by the VC computing device, from the payment processing network, the transaction data extracted from a data message transmitted over the payment processing network in response to a payment card transaction associated with a purchase made for the patient;
comparing, by the VC computing device, the received sensor data and the retrieved transaction data to the fulfillment condition to determine that the fulfillment condition has occurred; and
recording, by the VC computing device, in the task database, the task as fulfilled based on the determination that the fulfillment condition has occurred.

15. The computer-implemented method of claim 14, further comprising:
determining, by the VC computing device, that the task is overdue based on the fulfillment condition not having occurred by the time deadline corresponding to the task; and
generating, by the VC computing device, at least one of an audio alert and a text alert based on the determination that the task is overdue.

16. The computer-implemented method of claim 14, wherein receiving the task data comprises receiving, by the VC computing device, the task data via a user input at a user device.

17. The computer-implemented method of claim 16, further comprising providing, by the VC computing device, at the user device, a user interface for submitting task data.

18. The computer-implemented method of claim 14, wherein receiving the task data comprises receiving, by the VC computing device, the task data from the at least one sensor.

19. The computer-implemented method of claim 14, wherein retrieving the transaction data comprises retrieving transaction data processed over the payment processing network that is in communication with the at least one processor, and parse the transaction data to identify a merchant involved in the transaction and the time when the transaction occurred.

20. At least one non-transitory computer-readable media having computer-executable instructions embodied thereon, wherein when executed by a virtual caregiver (VC) computing device including at least one processor in communication with at least one memory device, at least one sensor and a payment processing network, the computer-executable instructions cause the at least one processor to:
receive task data for a selected patient;
generate, based on the task data, a task to be performed by or behalf of the patient, the task data including a task identifier, a fulfillment condition, and a time deadline;
store the generated task linked to the patient in a task database;
receive sensor data, from the at least one sensor, the sensor data relating to the task;
retrieve transaction data from the payment processing network, the transaction data extracted from a data message transmitted over the payment processing network in response to a payment card transaction associated with a purchase made for the patient;

compare the received sensor data and the retrieved transaction data to the fulfillment condition to determine that the fulfillment condition has occurred; and record, in the task database, the task as fulfilled based on the determination that the fulfillment condition has occurred.

* * * * *